(12) United States Patent
Chewter et al.

(10) Patent No.: US 9,115,039 B2
(45) Date of Patent: Aug. 25, 2015

(54) PROCESS FOR THE PREPARATION OF OLEFINS

(75) Inventors: Leslie Andrew Chewter, Amsterdam (NL); Jose Atilio Quevedo Enriquez, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/597,488

(22) Filed: Aug. 29, 2012

(65) Prior Publication Data

US 2013/0225896 A1  Aug. 29, 2013

Related U.S. Application Data

(60) Provisional application No. 61/529,000, filed on Aug. 30, 2011.

(51) Int. Cl.
*C07C 1/22* (2006.01)
*C07C 1/20* (2006.01)
*C07C 4/06* (2006.01)

(52) U.S. Cl.
CPC ... *C07C 1/22* (2013.01); *C07C 1/20* (2013.01); *C07C 4/06* (2013.01); *C07C 2529/40* (2013.01); *C07C 2529/85* (2013.01)

(58) Field of Classification Search
USPC ........................................ 585/638–639; 502/6
See application file for complete search history.

(56) References Cited

U.S. PATENT DOCUMENTS

| 2,545,162 | A | * | 3/1951 | Heigl et al. ........................ 502/6 |
| 4,567,029 | A | | 1/1986 | Wilson et al. |
| 5,095,163 | A | * | 3/1992 | Barger .......................... 585/640 |
| 5,191,141 | A | * | 3/1993 | Barger et al. .................. 585/640 |
| 5,914,433 | A | * | 6/1999 | Marker ......................... 585/313 |
| 6,797,851 | B2 | * | 9/2004 | Martens et al. ............... 585/640 |
| 2007/0155999 | A1 | | 7/2007 | Pujado et al. |
| 2007/0203380 | A1 | | 8/2007 | Vora et al. |
| 2010/0261944 | A1 | * | 10/2010 | Nesterenko et al. .......... 585/641 |

FOREIGN PATENT DOCUMENTS

| CA | 1036573 | 8/1978 |
| WO | 2006020083 | 2/2006 |

OTHER PUBLICATIONS

Kelling, R., et al; "Development of a control concept for catalyst regeneration by coke combustion"; Chemical Engineering Science, vol. 83; pp. 138-148; 2012.

* cited by examiner

*Primary Examiner* — In Suk Bullock
*Assistant Examiner* — Sharon Pregler

(57) ABSTRACT

Process for the preparation of olefins comprising reacting an oxygenate and/or olefinic feed in a reactor in the presence of a molecular sieve catalyst to form a mixture which comprises olefins and at least partially coked catalyst;
  passing at least partially coked catalyst to a regenerator; introducing into the regenerator an oxygen-containing gas to regenerate the at least partially coked catalyst, thereby producing a gaseous mixture and at least partially regenerated catalyst; separating at least partially regenerated catalyst and at least part of the gaseous mixture; analysing the composition of the gaseous mixture to control the burning rate of the coke present on the at least partially coked catalyst in the regenerator by adjusting the mass flow rate of the oxygen-containing gas on the basis of the analysis of the gaseous mixture; and passing at least part of the at least partially regenerated catalyst back to the reactor.

10 Claims, 1 Drawing Sheet

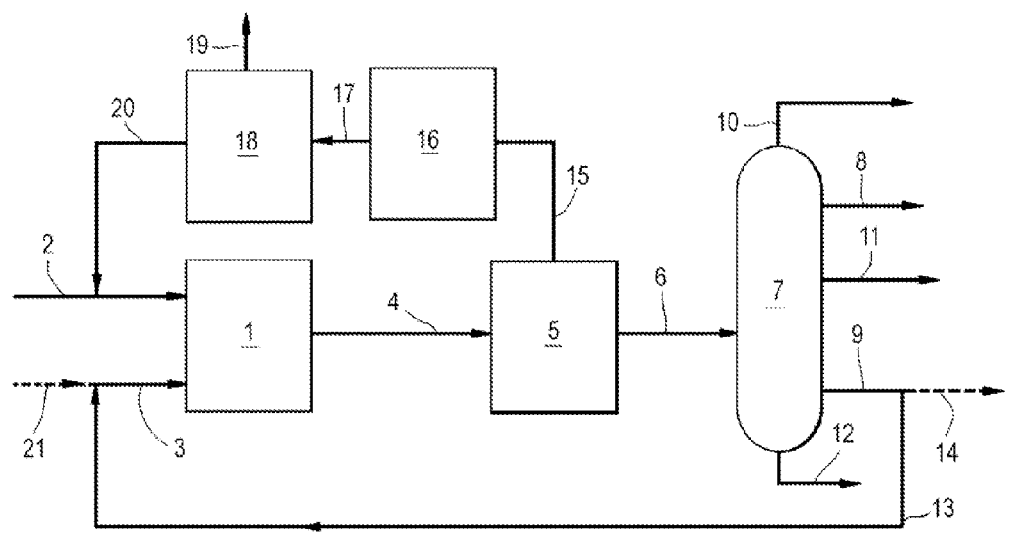

PROCESS FOR THE PREPARATION OF OLEFINS

The present application claims priority to Provisional Application 61/529,000, filed Aug. 30, 2011, which is incorporated herein by reference.

FIELD OF THE INVENTION

This invention relates to a process for the preparation of olefins such as ethylene and propylene. More in particular this invention relates to a process for the conversion of oxygenates into olefins.

BACKGROUND OF THE INVENTION

Processes for the preparation of olefins are known in the art.

U.S. Pat. No. 6,797,851 describes a process for making ethylene and propylene from an oxygenate feed using two or more zeolite catalysts.

In a first stage, an oxygenate feed is contacted with a first zeolite catalyst containing ZSM-5. The resulting conversion product contains an olefins composition. The olefin composition from the conversion reaction, with or without prior separation of ethylene and propylene, is then contacted with another zeolite catalyst in a second stage. The catalyst of such second stage is a one-dimensional zeolite having 10-membered ring channels, including ZSM-22, ZSM-23, ZSM-35, ZSM-42 or mixtures thereof. The eventual product comprises ethylene, propylene and C4+ olefins. The C4+ olefins may be partly recycled to the first stage as olefinic co-feed of the oxygenate feed. In the only example, pure methanol is converted by a two-step process into several olefins. In the process, typically use is made of a single reactor with a stacked bed configuration wherein the first stage is carried out in a first zeolite catalyst bed and the second stage is carried out a second zeolite bed (see FIG. 1 of U.S. Pat. No. 6,797,851). Alternatively, the two stages are carried out in two separate reactors (see FIGS. 2-5 of U.S. Pat. No. 6,797,851). The catalyst used in this process can be regenerated to remove carbonaceous deposits (coke) from the catalysts used. In case a single reactor is used this can be done periodically by ceasing the flow of feed to the reactor, introducing a regeneration medium, ceasing flow of the regeneration medium, and then reintroducing the feed to regenerated catalyst. In case two separate reactor are used regeneration will occur periodically or continuously outside the reactor by removing a portion of the deactivated catalyst to a separate regenerator. When the catalysts in both the two separate reactors need to be regenerated two separate regenerators are used.

During the regeneration, coke is removed from the catalyst. The extent to which coke is removed from the catalyst is an important feature of the process. If insufficient coke is removed, the selectivity of the oxygenate conversion is affected. However, exposing the catalyst to conditions that remove more coke may lead to an undesired reduction of the catalyst activity.

It would be desirable to have an improved process, in which olefins, such as ethylene and/or propylene, can be prepared in a single reaction stage which can be operated highly efficiently and in a cost-effective manner, with an improved control of the extent of coke removal from the catalyst.

SUMMARY OF THE INVENTION

A process is now proposed wherein use is made of a single reactor stage which is integrated with a regeneration stage wherein the regeneration of the catalyst is carried out in a manner that allows control of the coke burn-off during regeneration of the catalyst.

Accordingly, the present invention provides a process for the preparation of olefins, which process comprises the steps of:

(a) reacting an oxygenate and/or olefinic feed in a reactor in the presence of a molecular sieve catalyst to form a mixture which comprises olefins and at least partially coked catalyst;

(b) separating olefins and at least partially coked catalyst as obtained in step (a);

(c) recovering olefins obtained in step (b);

(d) passing at least partially coked catalyst as obtained in step (b) to a regenerator;

(e) introducing into the regenerator an oxygen-containing gas to regenerate at least part of the at least partially coked catalyst, thereby producing a gaseous mixture and at least partially regenerated catalyst;

(f) separating at least partially regenerated catalyst and at least part of the gaseous mixture as obtained in step (e);

(g) analysing the composition of the gaseous mixture as obtained in step (e) to control the burning rate of the coke present on the at least partially coked catalyst in the regenerator by adjusting the mass flow rate of the oxygen-containing gas as introduced in step (e) on the basis of the analysis of the gaseous mixture; and (h) passing at least part of the at least partially regenerated catalyst as obtained in step (f) to the reactor in step (a).

The process according to the present invention provides a very efficient and cost-effective overall process for the preparation of olefins such as ethylene and propylene.

BRIEF DESCRIPTION OF THE DRAWINGS

FIG. 1 shows schematically an embodiment of the present invention.

DETAILED DESCRIPTION OF THE INVENTION

In the present invention, an oxygenate feed is converted in an oxygenate-to-olefins (OTO) process or an olefinic feed is converted in an olefin cracking process (OCP).

The present invention in particular relates to a process for the conversion of oxygenates into olefins.

In step (a), an oxygenate and/or olefinic feed is reacted in a reactor in the presence of a molecular sieve catalyst to form a mixture which comprises olefins and at least partially coked catalyst. The reactor in step (a) can be an OTO reaction zone wherein the oxygenate feed is contacted with an oxygenate conversion catalyst under oxygenate conversion conditions, to obtain a conversion effluent comprising lower olefins. Reference herein to an oxygenate feed is to an oxygenate-comprising feed. In the OTO reaction zone, at least part of the feed is converted into a product containing one or more olefins, preferably including lower olefins, in particular ethylene and typically propylene.

The oxygenate used in the process according to the invention is preferably an oxygenate which comprises at least one oxygen-bonded alkyl group. The alkyl group preferably is a C1-C5 alkyl group, more preferably C1-C4 alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenate feed include alcohols and ethers. Examples of preferred oxygenates include alcohols, such as methanol, ethanol, propanol; and dialkyl ethers, such as dimethylether, diethylether, methylethylether. Preferably, the oxygenate is methanol or dimethylether, or a mixture thereof. More preferably, the oxygenate comprises methanol or dimethylether.

Preferably the oxygenate feed comprises at least 50 wt % of oxygenate, in particular methanol and/or dimethylether, based on total hydrocarbons, more preferably at least 70 wt %.

The oxygenate feed can comprise an amount of diluent, such as nitrogen and water, preferably in the form of steam. In one embodiment, the molar ratio of oxygenate to diluent is between 10:1 and 1:10, preferably between 4:1 and 1:2, in particular when the oxygenate is methanol and the diluent is water (steam).

A variety of OTO processes is known for converting oxygenates such as for instance methanol or dimethylether to an olefin-containing product, as already referred to above. One such process is described in WO-A 2006/020083. Processes integrating the production of oxygenates from synthesis gas and their conversion to light olefins are described in US20070203380A1 and US20070155999A1.

Catalysts suitable for converting the oxygenate feed in accordance with the present invention include molecular sieve-catalysts. The molecular sieve catalyst suitably comprises one or more zeolite catalysts and/or one or more SAPO catalysts. Molecular sieve catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieve catalysts preferably have a molecular framework of one, preferably two or more corner-sharing $[TO_4]$ tetrahedral units, more preferably, two or more $[SiO_4]$, $[AlO_4]$ and/or $[PO_4]$ tetrahedral units. These silicon, aluminum and/or phosphorous based molecular sieves and metal containing silicon, aluminum and/or phosphorous based molecular sieves have been described in detail in numerous publications including for example, U.S. Pat. No. 4,567,029. In a preferred embodiment, the molecular sieve catalysts have 8-, 10- or 12-ring structures and an average pore size in the range of from about 3 Å to 15 Å.

Suitable molecular sieve catalysts are silicoaluminophosphates (SAPO), such as SAPO-17, -18, -34, -35, -44, but also SAPO-5, -8, -11, -20, -31, -36, -37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Preferably, the conversion of the oxygenate feed may be accomplished by the use of an aluminosilicate-comprising catalyst, in particular a zeolite-comprising catalyst. In a zeolite-comprising catalyst the amount of zeolite is suitably from 20 to 50 wt %, preferably from 35 to 45 wt %, based on total catalyst composition.

Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type such as SSZ-44 and the EU-2 type, such as ZSM-48.

Aluminosilicates-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a Silica-to-Alumina ratio (SAR) of at least 60, preferably at least 80.

Particular catalysts include catalysts comprising one or more zeolite having one-dimensional 10-membered ring channels, i.e. one-dimensional 10-membered ring channels, which are not intersected by other channels.

Preferred examples are zeolites of the MTT and/or TON type.

In a preferred embodiment the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may comprise phosphorus as such, i.e. in elemental form, or in a compound, i.e. phosphorous other than any phosphorus included in the framework of the molecular sieve. It is preferred that an MEL or MFI-type zeolites comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05-10 wt % based on the weight of the formulated catalyst. A particularly preferred catalyst comprises phosphor and MEL or MFI-type zeolites having SAR of in the range of from 60 to 150, more preferably of from 80 to 100. An even more particularly preferred catalyst comprises phosphorus and ZSM-5 having SAR of in the range of from 60 to 150, more preferably of from 80 to 100. A further particularly preferred catalyst comprises phosphorus-treated MEL or MFI-type zeolites having SAR of in the range of from 60 to 150, more preferably of from 80 to 100. An even more particularly preferred catalyst comprises phosphorus-treated ZSM-5 having SAR of in the range of from 60 to 150, more preferably of from 80 to 100.

It is preferred that the molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. It is well known in the art how to produce such molecular sieves in the hydrogen form.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. Spherical particles are normally obtained by spray drying. Preferably the average particle size is in the range of 1-500 μm, preferably 50-100 μm.

The reaction conditions of the oxygenate conversion in step (a) include a reaction temperature of 350 to 1000° C., suitably from 350 to 750° C., preferably from 450 to 750° C., more preferably from 450 to 700° C., even more preferably 500 to 650° C.; and a pressure suitably from 1 bara to 50 bara, preferably from 1-15 bara, more preferably from 1-4 bara, even more preferably from 1.1-3 bara, and most preferably in from 1.3-2 bara.

Suitably, the oxygenate-comprising feed is preheated to a temperature in the range of from 120 to 550° C., preferably 250 to 500° C. prior to contacting with the molecular sieve catalyst in step (a).

Preferably, in addition to the oxygenate, an olefinic co-feed is provided along with and/or as part of the oxygenate feed. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon species. The olefinic co-feed can also comprise propylene.

The reaction in step (a) may suitably be operated in a fluidized bed, e.g. a dense, turbulent or fast fluidized bed or a riser reactor or a downward reactor system, and also in a fixed bed reactor, moving bed reactor or a tubular reactor. A fluidized bed, e.g. a turbulent fluidized bed, fast fluidized bed or a riser reactor system are preferred. These could be arranged in a single or multiple reactors arranged in parallel or in series.

The superficial velocity of the gas components in a dense fluidized bed will generally be from 0 to 1 m/s; the superficial velocity of the gas components in a turbulent fluidized bed will generally be from 1 to 3 m/s; the superficial velocity of the gas components in a fast fluidized bed will generally be from 3 to 5 m/s; and the superficial velocity of the gas components in a riser reactor will generally be from 5 to about 25 m/s.

It will be understood that dense, turbulent and fast fluidized beds will include a dense lower reaction zone with densities generally above 300 kg/m$^3$. Moreover, when working with a fluidized bed several possible configurations can be used: (a) co-current flow meaning that the gas (going upward) and the catalyst travels through the bed in the same direction, and (b) countercurrent, meaning that the regenerated catalyst is fed at the top of the bed and travels through the bed in opposite direction with respect to the gas, whereby the spent catalyst leaves the vessel at the bottom. In a conventional upward riser reactor system the catalyst and the vapors will travel co-currently.

More preferably, a fluidized bed, in particular a turbulent fluidized bed system is used. Suitably, in such a moving bed reactor the oxygenate feed is contacted with the molecular sieve catalyst at a weight hourly space velocity of at least 1 hr$^{-1}$, suitably from 1 to 1000 hr$^{-1}$, preferably from 1 to 500 hr$^{-1}$, more preferably 1 to 250 hr$^{-1}$, even more preferably from 1 to 100 hr$^{-1}$, and most preferably from 1 to 50 hr$^{-1}$.

The reactor in step (a) can also be an OCP reaction zone wherein the olefinic feed is contacted with an olefin conversion catalyst under olefin conversion conditions, to obtain a conversion effluent comprising lower olefins.

Suitably, the olefinic feed comprises C4+ olefins that will be converted to ethylene and/or propylene by contacting such a feed with a zeolite-comprising catalyst. Preferably, the olefinic feed is contacted with the zeolite-comprising catalyst in step (a) at a reaction temperature of 350 to 1000° C., preferably from 375 to 750° C., more preferably 450 to 700° C., even more preferably 500 to 650° C.; and a pressure from 1 bara to 50 bara, preferably from 1-15 bara. Optionally, such the olefinic feed also contains a diluent. Examples of suitable diluents include, but are not limited to, such as water or steam, nitrogen, paraffins and methane. Under these conditions, at least part of the olefins in the olefinic feed are converted to further ethylene and/or propylene.

In an OCP suitably aluminosilicate catalysts are used. Aluminosilicate catalysts, and in particular zeolite catalysts, have the additional advantage that in addition to the conversion of methanol or dimethylether, these catalysts also induce the conversion of olefins to ethylene and/or propylene. Therefore, aluminosilicate catalysts, and in particular zeolite catalysts, are particularly suitable for use as the catalyst in an OCP. Particular preferred catalyst for the OCP reaction are catalysts comprising at least one zeolite selected from MFI, MEL, TON and MTT type zeolites, more preferably at least one of ZSM-5, ZSM-11, ZSM-22 and ZSM-23 zeolites.

Also an OCP process may suitably be operated in a fluidized bed, e.g. a fast fluidized bed or a riser reactor or a downward reactor system, and also in a fixed bed reactor, moving bed reactor or a tubular reactor. A fluidized bed, e.g. a fast fluidized bed or a riser reactor system are preferred.

In step (b), olefins and at least partially coked catalyst as obtained in step (b) are separated. The separation in step (b) can be carried out by one or more cyclone separators. Such one or more cyclone separators may be located inside, partly inside and partly outside, or outside the reactor used in step (a). Such cyclone separators are well known in the art. Cyclone separators are preferred, but also methods for separating the catalyst from the olefins can be used that apply plates, caps, elbows, and the like.

In step (c), the olefins obtained in step (b) are recovered. Suitably, the olefins as recovered in step (c) are separated into at least one olefinic product fraction containing ethylene and/or propylene and one or more further olefinic fractions containing olefins having 4 or more carbon atoms, which further olefinic fraction(s) is (are) at least partly recycled to step (a) for use as an olefinic co-feed.

Preferably, at least 70 wt % of the olefinic co-feed, during normal operation, is formed by the recycle stream of the one or more further olefinic fractions containing olefins having 4 or more carbon atoms, preferably at least 90 wt % of olefinic co-feed, based on the whole olefinic co-feed, is formed by such a recycle stream. In order to maximize production of ethylene and propylene, it is desirable to maximize the recycle of C4 olefins in the effluent of the OTO process or olefin cracking process. This can be done by recycling at least part of the one or more further olefinic fractions containing olefins having 4 or more carbon atoms, preferably the C4-C5 hydrocarbon fraction, more preferably the C4 hydrocarbon fraction, to the OTO or OCP reaction zone in step (a). Suitably, however, a certain part thereof, such as between 1 and 5 wt %, is withdrawn as purge, since otherwise saturated hydrocarbons, in particular C4's (butane) would build up in the process, which are substantially not converted under the OTO or OCP reaction conditions.

The preferred molar ratio of oxygenate in the oxygenate feed to olefin in the olefinic co-feed provided to the OTO reaction zone in step (a) depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5, still more preferably in the range of 15:1 to 1:3, even still more preferably in the range of 12:1 to 1:3.

Although the one or more further olefinic fractions containing olefins having 4 or more carbon atoms as separated from the olefins as recovered in step (b) may be recycled as an olefinic co-feed to the OTO reaction zone in step (a), alternatively at least part of the olefins in these one or more further olefinic fractions may be converted to ethylene and/or propylene by contacting such C4+ hydrocarbon fraction in a separate unit with a zeolite-comprising catalyst. Such a separate process step directed at converting C4+ olefins to ethylene and propylene is, as will be clear from the foregoing, also referred to as an olefin cracking process (OCP) and the described preferences provided hereon above for an OCP also apply here.

This step is particularly preferred when the molecular sieve catalyst in step (a) comprises a least one SAPO, AlPP, or MeAlPO type molecular sieve, preferably SAPO-34. These catalysts are less suitable for converting olefins. Preferably, the C4+ hydrocarbon fraction is contacted with the zeolite-comprising catalyst at a reaction temperature of 350 to 1000° C., preferably from 375 to 750° C., more preferably 450 to 700° C., even more preferably 500 to 650° C.; and a pressure from 1 bara to 50 bara, preferably from 1-15 bara. Optionally, such a stream comprising C4+ olefins also contains a diluent. Examples of suitable diluents include, but are not limited to, such as water or steam, nitrogen, paraffins and methane. Under these conditions, at least part of the olefins in the C4+ hydrocarbon fraction are converted to further ethylene and/or propylene. The further ethylene and/or propylene may be combined with the further ethylene and/or propylene as obtained in step (a). In the subsequent OCP, suitably, aluminosilicate catalysts are used. Aluminosilicate catalysts, and in particular zeolite catalysts, have the additional advantage that in addition to the conversion of methanol or dimethylether, these catalysts also induce the conversion of olefins to ethylene and/or propylene. Therefore, aluminosilicate catalysts, and in particular zeolite catalysts, are particularly suitable for use as the catalyst in the subsequent OCP. Particular preferred catalyst for the subsequent OCP reaction, i.e. converting part of the obtained olefins, and preferably part of the C4+ hydrocarbon fraction of the obtained olefins, are catalysts comprising at least one zeolite selected from MFI, MEL, TON and MTT type zeolites, more preferably at least one of ZSM-5, ZSM-11, ZSM-22 and ZSM-23 zeolites. Preferably, these catalysts are modified with phosphorus as described herein above for MFI and MEL-comprising catalyst.

Also the subsequent OCP process may suitably be operated in a fluidized bed, e.g. a fast fluidized bed or a riser reactor or downward reactor system, and also in a fixed bed reactor, moving bed reactor or a tubular reactor. A fluidized bed, e.g. a fast fluidized bed or a riser reactor system are preferred.

The mixture comprising olefins and catalyst obtained from the process in step (a) comprises ethylene and/or propylene, which may be separated from the remainder of the components in the mixture comprising olefins and catalyst. The olefinic product comprises advantageously at least 50 mol %, in particular at least 50 wt %, ethylene and propylene, based on total hydrocarbon content in the mixture comprising olefins and catalyst.

When the mixture comprising olefins and catalyst obtained in step (a) comprises ethylene, at least part of the ethylene may be further converted into at least one of polyethylene, mono-ethylene-glycol, ethylbenzene and styrene monomer. When the mixture comprising olefins and catalyst obtained in step (a) comprises propylene, at least part of the propylene may be further converted into at least one of polypropylene and propylene oxide.

Preferably, the olefins as recovered in step (b) are subjected to a quenching treatment before they are separated into at least one olefinic product fraction containing ethylene and/or propylene and one or more further olefinic fractions. In such a quenching treatment water and C6+ hydrocarbons can be removed from the olefins are subjected to a fractionating treatment to separate the olefins into at least one olefinic product fraction containing ethylene and/or propylene and one or more further olefinic fractions.

Suitably, the olefins are subjected to a heat recovery step before they are subjected to the quenching treatment.

More preferably, olefins obtained after the quenching treatment are first compressed before they are separated into at least one olefinic product fraction containing ethylene and/or propylene and one or more further olefinic fractions.

Instead of a quenching treatment of the olefins, also use can be made of air coolers to bring down the temperature of the olefins.

In step (d) at least partially coked catalyst as obtained in step (b) is passed to a regenerator. Suitably, the at least partially coked catalyst as obtained in step (b) is passed in its entirety to the regenerator. The molecular sieve catalyst to be used in accordance with the present invention deactivates in the course of the process with time, amongst others due to coke deposition on the catalyst. Coke herein refers to a carbonaceous composition which next to the prevailing carbon may also contain hydrogen and other elements. Hence, the molecular sieve catalyst needs to be regenerated in order to at least partly remove coke from the coked catalyst as obtained in step (a). Conventional catalyst regeneration techniques can be employed to remove the coke. It is not necessary to remove all the coke from the catalyst as it is believed that a preset amount of residual coke may enhance the catalyst performance and additionally, it is believed that complete removal of the coke may also lead to degradation of the molecular sieve.

In order to regenerate at least part of the at least partially coked catalyst an oxygen-containing gas is introduced in the regenerator in step (e), thereby producing a gaseous mixture and at least partially regenerated catalyst. The oxygen-containing gas may be chosen from oxygen and air. Also mixtures can suitably be used of these oxygen-containing gases. Preferably, the oxygen-containing gas comprises oxygen, more preferably air is used as the oxygen-containing gas. In specific applications, it may be preferred to increase the oxygen content of air by adding an oxygen stream or removing nitrogen from the air, with the purpose of establishing an appropriate heat balance.

Suitably, the volume of oxygen in the oxygen-containing gas as introduced in step (b) is 15-50 mol-%, preferably 18-35 mol-%, based on total volume of the oxygen-containing gas.

Generally, the mass flow rate of the oxygen-containing gas may be adjusted in such a way that it satisfies the coke burn requirements from a mass balance perspective.

The amount of oxygen containing gas will be determined by the amount of coke to be removed from the catalyst and the combustion mode as applied in the regenerator. For example, if it is a partial burn mode, then additional oxygen containing gas will be required downstream of the regenerator in the CO boiler to complete the combustion of the CO into $CO_2$. CO cannot be released into the environment, hence, all plants will have to fully convert the CO into $CO_2$ at the end. Partial combustion mode is preferred because it allows a high level of coke on regenerated catalyst. Full combustion mode is not preferred because it would leave a very small amount of residual coke on regenerated catalyst.

In step (e), the regeneration is carried out under conditions of temperature, pressure and residence time that is usually applied in regeneration processes to burn coke from catalysts. Suitably, between 0.01-5 wt % of the coke present on the at least partially coked catalyst is removed from the catalyst during regeneration.

Suitably, the regeneration in step (e) is carried out at a temperature in the range of from 580-800° C., preferably in the range of from 600-750° C., more preferably in the range of from 620-680° C., and a pressure in the range of from 1-5 bara, preferably in the range of from 1-3 bara, more preferably in the range of from 1.3-2 bara. The regeneration can suitably be carried out in a fixed bed, a fluidized bed such as a dense, turbulent or fast fluidized bed, or in a riser or downward regenerator. Preferably, the regeneration is carried out in a turbulent fluidized bed.

Suitably, the regeneration in step (e) can be carried out in a periodical manner or continuous manner. Preferably, the regeneration in step (e) is carried out in a continuous manner.

The residence time of the molecular sieve catalyst in the regenerator can suitably be in the range of from one minute to several hours. Preferably, the residence time is from 1 to 100 minutes. More preferably, the residence time of the catalyst in the regenerator is in the range of from 1-60 minutes, most preferably in the range of from 2-15 minutes.

Suitably, after step (b) the at least partially coked catalyst can be subject to a stripping treatment before it is passed to the regenerator in step (d). In such a stripping treatment a stripping gas can be used to remove organic compounds, such as non-separated olefins, from the catalyst before it is passed to the regenerator.

In step (f), at least partially regenerated catalyst and at least part of the gaseous mixture as obtained in step (e) are separated. Typically, at least partially regenerated catalyst exits the regenerated at the bottom end, while the gaseous mixture is recovered at the top end of the regenerator. The catalyst exiting the regenerator is typically stripped to remove oxygen and other gaseous components in the gaseous mixture. Some catalyst may be entrained in the gaseous mixture and may be separated from the gaseous mixture. The latter part of the separation in step (f) can be carried out by one or more cyclone separators. Such one or more cyclone separators may be located inside, partly inside and partly outside, or outside the regenerator. Such cyclone separators are well known in the art. Cyclone separators are preferred, but also methods for separating the catalyst from flue gas can be used that apply plates, caps, elbows, and the like.

In step (g), the composition of the gaseous mixture as obtained in step (e) is analysed to control the burning rate of the coke present on the at least partially coked catalyst in the regenerator. Reference herein to the burning rate is the mass of coke removed per hour ($kg_{coke}$/hour). The burning rate of the coke is controlled by adjusting the mass flow rate of the oxygen-containing gas as introduced in step (e) on the basis of the analysis in step (g) of the gaseous mixture as obtained in step (e). In this way the level of coke on the catalyst to be passed to the reactor in step (h) can attractively be controlled. Changes in the operating conditions in the regenerator may influence the burning rate of the coke in the regenerator which may affect the overall process performance and the catalyst lifetime. Such operating conditions include the catalyst circulation time, the pressure balance in the regenerator, heat losses, the amount of coke present on the catalyst, the regeneration temperature, and the level of the catalyst bed in the regenerator. By means of step (g) the burning rate of the coke can be controlled and optimized against changing operating conditions in the regenerator. Moreover, on the basis of the mass flow rate of the oxygen-containing gas and the analysis of the least partially regenerated catalyst, and the amount of steam in the flue gas, the heat released during the regeneration can be determined, and a more direct heat control inside the regenerator can be established. In this way the overall process performance in terms of capacity and, for example, catalyst lifetime can be improved.

A sample of the gaseous mixture as obtained in step (e) can be taken from inside the regenerator or downstream the regenerator and its composition can be analysed externally. It is also possible to analyse the composition of the gaseous mixture as obtained in step (f). In another embodiment it is possible to analyse the composition of a sample of the gaseous mixture taken inside the regenerator as well as to analyse the composition of the gaseous mixture as obtained in step (f).

Suitably, in the analysis in step (g) the concentration of carbon monoxide present in the gaseous mixture is determined and the burning rate of the coke present on the at least partially coked catalyst is controlled by adjusting the mass flow rate of the oxygen-containing gas as introduced in step (e) on the basis of the concentration of carbon monoxide present in the analysed gaseous mixture. The carbon monoxide present in the gaseous mixture results from the partial combustion of coke present on the at least partially coked catalyst.

The concentration of the carbon monoxide can suitably be determined by well-known means such as absorption spectroscopy, gas chromatography, infrared absorption spectroscopy, non-dispersive infrared analysis among others. It is further observed that that the amount of $H_2O$, $CO_2$ and $O_2$ can be determined also with these methods and they can be used for analysing the flue gas composition in order to close the mass and energy balances in the regenerator.

In another embodiment of the present invention in the analysis in step (g) the concentration of oxygen present in the gaseous mixture is determined by continuous emission monitoring, e.g. with a ZrO2 oxygen analyser, and the burning rate of the coke present on the at least partially coked catalyst is controlled by adjusting the mass flow rate of the oxygen-containing gas as introduced in step (e) on the basis of the concentration of oxygen present in the analysed gaseous mixture. The oxygen present in the gaseous mixture, preferably present in the range from 0.5 to 5%, results from the full combustion of coke present on the at least partially coked catalyst.

Moisture measurements to measure water on-line can be done as well, before and after combustion.

In another embodiment of the present invention in the analysis in step (g) the concentrations of carbon monoxide and oxygen present in the gaseous mixture are determined and the burning rate of the coke present on the at least partially coked catalyst is controlled by adjusting the mass flow rate of the oxygen-containing gas as introduced in step (e) on the basis of the concentrations of carbon monoxide and oxygen present in the analysed gaseous mixture.

In another embodiment of the present invention in the analysis in step (g) the concentrations of carbon monoxide, carbon dioxide and oxygen present in the gaseous mixture are determined and the burning rate of the coke present on the at least partially coked catalyst is controlled by adjusting the mass flow rate of the oxygen-containing gas as introduced in step (e) on the basis of the concentrations of carbon monoxide, carbon dioxide and oxygen present in the analysed gaseous mixture.

In yet another embodiment of the present invention in the analysis in step (g) the concentrations of carbon monoxide, carbon dioxide, water and oxygen present in the gaseous mixture are determined and the burning rate of the coke present on the at least partially coked catalyst is controlled by adjusting the mass flow rate of the oxygen-containing gas as introduced in step (e) on the basis of the concentrations of carbon monoxide, carbon dioxide, water and oxygen present in the analysed gaseous mixture.

The embodiments as described hereinabove, wherein the concentration of oxygen in the gaseous mixture is determined are especially attractive when the regenerator is operated in a full combustion mode of operation, resulting in a complete oxidation of carbon monoxide and also full regeneration of catalyst inside the regenerator.

When the regenerator is operated in a partial burn mode it will be sufficient to determine only the concentration of carbon monoxide in the gaseous mixture as obtained in step (e).

The analysis of the gaseous mixture can be done by hand using a gas analyser, e.g. such as those provided by Drager™, or by way of an automated analysis tool incorporated in the gas analyzers.

Preferably, the mass flow rate of the oxygen-containing gas as introduced in step (e) is automatically adjusted on the basis of the analysis of the gaseous mixture. Suitably this can be established by means of a flow control valve placed in the air line source, a compressor inlet guide vane opening or indirectly by adjusting the revolutions of a centrifugal compressor by adjusting the steam flow to the turbine coupled to the compressor.

In step (h), at least part of the at least partially regenerated catalyst as obtained in step (f) is passed to the reactor in step (a).

Since the burning of coke is an exothermic reaction, the temperature of the catalyst exiting the regenerator needs to be adjusted to the reactor requirements. This can be done in various ways. Suitably, at least part of the at least partially regenerated catalyst as obtained in step (f) is passed through a catalyst cooler before it is passed to the reactor in step (a). In this way the temperature of the at least partially regenerated catalyst can be controlled before it is passed to the reactor in step (a). The catalyst cooler may be a heat exchanger that is located either inside, partly inside and partly outside, or outside the regenerator. The cooled and at least partially regenerated catalyst as obtained in the catalyst cooler can be returned to the regenerator in a continuous cycle. In another embodiment a portion of the cooled and at least partially regenerated catalyst as obtained in the catalyst cooler cooled is returned to the regenerator in a continuous cycle, whereas another portion of the cooled and at least partially regenerated catalyst as obtained in the catalyst cooler is passed to the reactor in step (a).

The reactor and regenerator can be arranged in such a way that the oxygenate and/or olefinic feed contacts the at least partially regenerated catalyst before it is passed to the reactor in step (a). The reactor and regenerator can also be arranged to allow that the oxygenate and/or olefinic feed contacts the at least partially regenerated catalyst after it is passed to the reactor in step (a).

The at least partially regenerated catalyst can be combined with a fresh molecular sieve catalyst before it is passed to the reactor in step (a). The at least partially regenerated catalyst can also be directly passed to the reactor in step (a), preferably after passing through a catalyst cooler.

The at least partially regenerated catalyst can be subject to a stripping treatment before it is passed to the reaction step. In such a stripping treatment, an inert stripping gas, such as steam or nitrogen, can be used to remove oxygen and other combustion products that might cause inconveniences in the reaction or in the products separation steps.

Suitably, a carrier, such as an inert gas, feedstock vapor, a hydrocarbon recycled stream or steam can be used semi-continuously or continuously to facilitate the introduction of the at least partially regenerated catalyst, into the reactor system. Compressed air, nitrogen or steam will be used for transporting the fresh catalyst from the fresh catalyst storage vessel into the regenerator.

The mass flow rate of the at least partially regenerated catalyst to be passed to the reactor in step (a) can be used to control the optimum level of coke on the molecular sieve catalyst. The optimum level of coke on the molecular sieve catalyst can further be controlled by means of the coke combustion rate and the residence time of the catalyst in the regenerator.

The person skilled in the art will readily understand that many modifications may be made without departing from the scope of the present invention.

DETAILED DESCRIPTION OF THE DRAWINGS

FIG. 1 shows schematically an embodiment of the present invention. The person skilled in the art will readily understand that, while the present invention in some instances may have been illustrated making reference to a specific combination of features and measures, many of those features and measures are functionally independent from others features and measures given in the respective embodiment(s) such that they can be equally or similarly applied independently in other embodiments.

In FIG. 1, an oxygenate and/or olefinic feedstock as specified herein above is fed to a reactor 1 via line 2. An olefinic co-feed, as specified herein above, is fed to the reactor as well, via line 3. In the reactor system 1, the oxygenate and/or olefinic feedstock and the olefinic co-feed are allowed to react in the presence of an oxygenate or olefin conversion catalyst as specified herein above, to prepare a mixture comprising olefins and at least partially coked catalyst. The olefins and portions of the at least partially coked catalyst are passed via line 4 to a cyclone separator 5 in which olefins are separated from the at least partially coked catalyst. The olefins are recovered and passed via line 6 to a fractionation section 7. In this embodiment the fractionation section is shown to produce an ethylene-rich product stream in line 8 as light olefinic fraction, and a C4-olefin-rich stream in line 9, as heavier olefinic fraction specified herein above, and further a lighter stream in overhead line 10 comprising lighter contaminants such as methane, light hydrocarbons and/or inerts, a propylene-rich stream in line 11 and a C5+ hydrocarbon rich stream in line 12.

At least part of the heavier olefinic fraction in line 9 is recycled via line 13 to an inlet of the reactor 1, to form at least part of the olefinic co-feed. If desired, part of the heavier olefinic fraction can be withdrawn via line 14. If this is merely a small bleed stream, such as less than 10 wt % or in particular less than 5 wt %, substantially all of the heavier olefinic fraction is considered to be recycled. To the recycle stream other components can be blended, such as from the propylene rich stream 11 or from the C5+ hydrocarbon-rich stream 12. The latter can increase yield of lower olefins, but is less desired because it does so at the cost of ethylene selectivity.

From the cyclone separator 5 the at least partially coked catalyst which is separated from the olefins is passed via line 15 to a regenerator 16 in which the catalyst is thereby producing a gaseous mixture and an at least partially regenerated catalyst. The gaseous mixture and the at least partially regenerated catalyst are then passed via a line 17 to a cyclone separator 18, wherein the at least partially regenerated catalyst and at least part of the gaseous mixture are separated. The gaseous mixture is withdrawn via line 19 and the at least partially regenerated catalyst is passed via line 20 to the reactor 1.

In special and not generally preferred embodiments, such as during start-up, part of the olefinic co-feed can be obtained from an external source via line 21. If that is not the case, the overall process converts oxygenate or C4+ olefins in line 2 to mainly light olefins in lines 8 and 11.

What is claimed is:

1. Process for the preparation of olefins, which process comprises the steps of:
   (a) reacting an oxygenate and/or olefinic feed in a reactor in the presence of a molecular sieve catalyst to form a mixture which comprises olefins and at least partially coked catalyst;
   (b) separating olefins and at least partially coked catalyst as obtained in step (a);
   (c) recovering olefins obtained in step (b);
   (d) passing at least partially coked catalyst as obtained in step (b) to a regenerator;
   (e) introducing into the regenerator an oxygen-containing gas to regenerate at least part of the at least partially coked catalyst in a partial burn mode, thereby producing a gaseous mixture and at least partially regenerated catalyst;
   (f) separating at least partially regenerated catalyst and at least part of the gaseous mixture as obtained in step (e);
   (g) analysing the composition of the gaseous mixture as obtained in step (e) to control the burning rate of the coke present on the at least partially coked catalyst in the regenerator by adjusting the mass flow rate of the oxygen-containing gas as introduced in step (e) on the basis of the analysis of the gaseous mixture such that between 0.01-5 wt% of the coke present on the at least partially coked catalyst is removed from the catalyst during regeneration; and
   (h) passing at least part of the at least partially regenerated catalyst as obtained in step (f) to the reactor in step (a).

2. Process according to claim 1, wherein the oxygenate comprises methanol or dimethylether.

3. Process according to claim 1, wherein the molecular sieve catalyst comprises one or more zeolite catalyst and/or one or more SAPO, ALPO and/or MeALPO catalysts.

4. Process according to claim 1, wherein the olefins as recovered in step (c) are separated into at least one olefinic product fraction containing ethylene and/or propylene and one or more further olefinic fractions containing olefins having 4 or more carbon atoms, which further olefinic fraction(s) is (are) at least partly recycled to step (a).

5. Process according to claim 1, wherein the molecular sieve catalyst comprises a phosphor-treated zeolite of the MFI type, preferably ZSM-5, having a silica-to-alumina ratio in the range of from 60 to 150.

6. Process according to claim 1, wherein the reaction in step (a) is conducted at a temperature from 350 to 750° C.; and a pressure of from 1-15 bara.

7. Process according to claim 1, wherein the regeneration in step (e) is carried out at a temperature in the range of from 580-800° C.; and a pressure in the range of from 1-5 bara.

8. Process according to claim 1, wherein in the analysis in step (g) the concentration of carbon monoxide present in the gaseous mixture is determined and the burning rate of the coke present on the at least partially coked catalyst is controlled by adjusting the mass flow rate of the oxygen-containing gas as introduced in step (e) on the basis of the concentration of carbon monoxide present in the analysed gaseous mixture.

9. Process according to claim 1, wherein in the analysis in step (g) the concentration of oxygen present in the gaseous mixture is determined and the burning rate of the coke present on the at least partially coked catalyst is controlled by adjusting the mass flow rate of the oxygen-containing gas as introduced in step (e) on the basis of the concentration of oxygen present in the analysed gaseous mixture.

10. Process according to claim 1, wherein the mass flow rate of the oxygen-containing gas as introduced in step (e) is automatically adjusted on the basis of the analysis of the gaseous mixture.

* * * * *